United States Patent [19]

Weis et al.

[11] Patent Number: 5,214,134
[45] Date of Patent: May 25, 1993

[54] PROCESS OF LINKING NUCLEOSIDES WITH A SILOXANE BRIDGE

[75] Inventors: Alexander L. Weis, Berwyn; Ashis K. Saha, Frazer, both of Pa.; Frederick H. Hausheer, San Antonio, Tex.

[73] Assignee: Sterling Winthrop Inc., New York, N.Y.

[21] Appl. No.: 581,502

[22] Filed: Sep. 12, 1990

[51] Int. Cl.$^5$ .................. C07H 19/173; C07H 19/073; C07H 21/04

[52] U.S. Cl. .................. 536/25.3; 536/25.31; 536/25.33; 536/25.34

[58] Field of Search .................. 536/27, 28, 29

[56] References Cited

U.S. PATENT DOCUMENTS 4,959,463 9/1990 Froehler et al. .................. 536/27

FOREIGN PATENT DOCUMENTS 3215693 9/1988 Japan .

OTHER PUBLICATIONS

Ogawa, *Nippon Nogei Kagaku Kaisha*, 52(7), R93–R101 (1978); see also *Chem. Abstr.*, 89:215,672u (1978).
Vroom et al., *Nucleic Acids Research*, 16(7),2987–3003 (1988).
Ishii et al., *J. Chromatography*, 218, 189–197 (1981).
Kochetkov et al., *Organic Chemistry of Nucleic Acids*, Part B, Plenum Press, New York, 1972, pp. 460–461.
Schneider et al., "Building Blocks for Oligonucleotide Analogs with Dimethylene-Sulfide, -Sulfoxide, and -Sulfone Groups Replacing Phosphodiester Linkages", *Tetrahedron Letters*, vol. 31, No. 3, pp. 335–338, 1990.
Ogilvie et al., "Synthesis of a Thymidine Dinucleotide Analogue Containing an Internucleotide Silyl Linkage", *Tetrahedron Letters*, vol. 26, No. 35, pp. 4159–4162, 1985.
Cormier et al., "Synthesis of Hexanucleotide Analogues Containing Diisopropylsilyl Internucleotide Linkages", *Nucleic Acids Research*, vol. 16, No. 10, pp. 4583–4594, 1988.

*Primary Examiner*—Johnnie R. Brown
*Assistant Examiner*—L. Eric Crane
*Attorney, Agent, or Firm*—Irving Newman

[57] ABSTRACT

A method of linking nucleosides with a siloxane bridge comprising reacting a 3'-silylated-5'-protected nucleoside with an unprotected nucleoside is disclosed. The silylated and unprotected nucleosides may be either monomeric nucleosides or the terminal nucleosides of an oligonucleotide or oligonucleotide analog. A method of synthesizing an oligonucleotide analog having siloxane internucleoside linkages is also disclosed. The method of synthesis comprises silylating a 5'-protected nucleoside with a bifunctional silylating reagent to form a 3'-silylated nucleoside, reacting the silylated nucleoside with an unprotected nucleoside in the presence of a base catalyst and repeating these steps to form an oligonucleotide analog. A modified solid phase synthesis method for preparing an oligonucleotide analog having siloxane internucleoside linkages is also disclosed.

24 Claims, No Drawings

PROCESS OF LINKING NUCLEOSIDES WITH A SILOXANE BRIDGE

FIELD OF THE INVENTION

The present invention relates to a method of linking nucleosides with a siloxane bridge comprising reacting a 3'-silylated nucleoside with an unprotected nucleoside. The present invention further relates to methods of synthesizing oligonucleotide analogs having at least one siloxane internucleoside bridge.

BACKGROUND OF THE INVENTION

The nucleic acids, RNA and DNA, represent naturally occurring oligonucleotides. As used herein, the term "oligonucleotide" means homopolymer or heteropolymer sequences of nucleosides in which the nucleosides are linked with a phosphodiester bridge.

Due to advances in chemical technology, oligonucleotides comprising several hundred nucleosides or bases can now be synthetically produced. *Oligonucleotide Synthesis: A Practical Approach*, ed. by M. J. Gait, IRL Press, Washington, D.C. (1984). Synthetic oligonucleotides have great scientific and therapeutic utility. Synthetic oligodeoxynucleotides, for example, have widespread use in the field of recombinant DNA. Gait, supra at 1. In recent years, synthetic oligonucleotides have been shown to have therapeutic potential as antisense agents to inhibit gene expression. Uhlman, E. and Peyman, A., *Chemical Reviews*, 90(4): 544–583 (1990).

An antisense agent is a compound that binds to or hybridizes with a nucleotide sequence in a target nucleic acid, RNA or DNA, to inhibit the function of said target nucleic acid. Because of their ability to hybridize with both RNA and DNA, antisense agents can interfere with gene expression at the level of transcription, RNA processing or translation.

At the present time, however, the development of practical scientific and therapeutic applications of antisense technologies is hampered by a number of technical problems. See e.g.; Klausner, A., *Biotechnology*, 8:303–304 (1990); Armstrong, L., *Business Week*, Mar. 5, 1990. Such problems include (1) degradation by endogenous nucleases, (2) the high cost of production, (3) lack of sequence specific hybridization to target nucleic acids, (4) nonuniformity due to the presence of chiral phosphorous centers and (5) inadequate delivery to desired targets, for example, due to inappropriate solubility coefficients, membrane transport and cellular tracking.

One approach to preparing antisense agents that are stable, nuclease resistant, inexpensive to produce and which can be delivered to and hybridize with nucleic acid targets throughout the body is to synthesize oligonucleotide analogs having modifications in the internucleoside bridges or linkages.

As used herein, the phrase "oligonucleotide analog" refers to homopolymer or heteropolymer sequences of nucleosides or analogs thereof with non-phosphodiester internucleoside linkages.

In general, two types of oligonucleotide analogs have been reported. The first type includes those having modified phosphate linkages. The second type includes those analogs having non-phosphate internucleoside linkages. Uhlmann, E., supra.

Representative non-phosphate internucleoside linkages include siloxane, carbamate, carboxymethyl esters, acetamidate, carbonate and thioethers. Uhlmann, supra.

Of particular relevance to the present invention is the siloxane linkage or bridge.

Nucleoside dimers and hexamers having siloxane internucleoside linkages and a method of synthesizing such polymers have been reported by Ogilvie and Cormier. See, e.g., Ogilvie, K. K. and Cormier, J. F., *Tetrahedron Letters*, 26(35):4159–4162 (1985); Cormier J. F. and Ogilvie, K. K., *Nucleic Acids Research*, 16(10):4583–4594 (1988).

According to this published method, a 5'-protected nucleoside is reacted with a silylating reagent to form a 3'-silylated nucleoside, which silylated nucleoside is then reacted with a protected nucleoside to produce a fully protected, 3',5'-silyl linked dinucleoside. The fully protected, silyl linked dinucleoside is then deprotected at either terminal to carry out chain extension via another round of coupling with protected nucleosides.

Certain problems are associated with this method. When this method is employed to synthesize nucleoside polymers, the desired end product is produced in low yields ranging from about 35% to about 46%. The low yield is attributed both to the production of undesired byproducts, in particular, the 3',3'-symmetrical dimer, Uhlman, E. supra at pg. 553, resulting from self conjugation of the nucleoside building blocks, and to significant loss of useful product resulting from polymer deprotection.

The present invention provides a method of linking nucleosides with a siloxane bridge while suppressing formation of the 3',3'-dimer. This method comprises reacting a silylated nucleoside with an unprotected nucleoside in the presence of a hindered base catalyst. The use of unprotected nucleosides as compared to the procedure of Ogilvie and Cormier, has the advantages of increasing both the yield of desired end-products and the efficiency of the synthesis (thereby reducing the cost).

A preferred embodiment of the present invention, in which the reaction is carried out in the presence of a sterically hindered base catalyst, provides the additional advantage that the formation of undesired 3',3'-symmetrical dimers is minimized.

SUMMARY OF THE INVENTION

The present invention provides a method of linking nucleosides with a siloxane bridge comprising reacting a 3'-silylated-5'-protected nucleoside with an unprotected nucleoside in the presence of a hindered base catalyst.

The siloxane bridge has the formula:

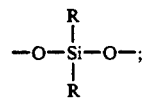

where R is independently $C_1$-$C_6$ alkyl. In a preferred embodiment, R is methyl or isopropyl.

Both the silylated nucleoside and the unprotected nucleoside may be either monomeric nucleosides or the 3' and 5' terminal nucleosides respectively of an oligonucleotide or oligonucleotide analog. Preferred monomeric nucleosides are thymidine, $N^6$-benzoyldeoxyadenosine, N⁴-benzoyldeoxycytidine and N²-isobutyldeoxyguanosine.

The reaction of the 3'-silylated-5'-protected nucleoside with the unprotected nucleoside preferably occurs in a neutral or alkaline, aprotic solution. In a preferred embodiment, the alkaline, aprotic solution comprises 2,6-di-tert-butyl-4-methylpyridine in a mixture of acetonitrile and dimethylformamide.

In another aspect, the present invention comprises a method of synthesizing an oligonucleotide analog having siloxane internucleoside linkages comprising the steps of:

a) silylating a 5'-protected nucleoside with a bifunctional silylating reagent to form a 3'-silylated-5'-protected nucleoside;

b) reacting the silylated nucleoside with an unprotected nucleoside; and c) repeating steps a) and b) to form said oligonucleotide analog.

Bifunctional silylating reagents utilized with the present invention have the formula I:

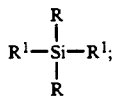

where R is independently $C_1$–$C_6$ alkyl; and $R^1$ is a leaving group. In a preferred embodiment, the silylating agent is symmetrical and R is isopropyl or methyl and $R^1$ is a leaving group such as Cl or $SO_2CF_3$.

Both the 5' protected nucleoside and the unprotected nucleoside are independently thymidine, N⁶-benzoyldeoxyadenosine, N⁴-benzoyldeoxycytidine or N²-isobutyldeoxyguanosine.

Preferably, both steps a) and b) occur in an alkaline, aprotic solution and, more preferably in a solution comprising 2,6-di-tert-butyl-4-methylpyridine in a mixture of acetonitrile and dimethylformamide, more preferably about a 1:1 (v/v) mixture of said solvents.

The present invention still further provides a solid phase method of synthesizing oligonucleotide analogs having siloxane internucleoside linkages comprising the steps of:

a) attaching a 5'-protected nucleoside to a solid support;

b) deprotecting the attached nucleoside;

c) reacting the deprotected nucleoside with a 3'-silylated-5'-protected nucleoside in the presence of a base catalyst and a neutral or basic aprotic solvent;

d) capping the unreacted nucleosides;

e) repeating steps b), c) and d) until an oligonucleotide analog of desired length is formed; and f) removing the formed oligonucleotide analog from the solid support.

The siloxane internucleoside linkages of the oligonucleotide analog have the formula II.

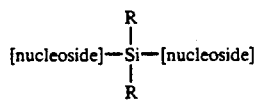

In the solid phase method, the base catalyst used in accordance with the present invention is preferably a hindered base and, more preferably 2,6-di-tert-butyl-4-methylpyridine. Generally, the base, imidazole, is also present as a stabilizer for the silylated intermediate. Its presence also helps to improve the yield. A preferred aprotic solvent is a mixture of acetonitrile and dimethylformamide, more preferably about a 1:1 (v/v) mixture. The formed oligonucleotide analog is preferably removed from the solid support by cleaving with aqueous ammonia in isopropanol and acetonitrile.

DETAILED DESCRIPTION OF THE INVENTION

Nucleosides linked with a siloxane bridge are synthesized by reacting a 3'-silylated-5'-protected nucleoside with an unprotected nucleoside.

Siloxane bridges contemplated by the present invention are dialkylsilyl linkages of the formula:

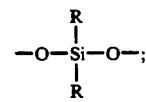

where each R is independently $C_1$–$C_6$ alkyl.

In a preferred embodiment, R is isopropyl or methyl.

The 3'-silylated-5'-protected nucleoside can be made in accordance with procedures known and readily apparent to those of skill in the art. In a preferred embodiment, a 3'-hydroxyl-5'-protected nucleoside is reacted with a bifunctional silylating reagent in an alkaline, aprotic solution. The protecting group at the 5'-carbon hydroxyl group is selected on the basis of its acid lability. Suitable protecting groups are known and readily apparent to those of skill in the oligonucleotide synthesis art. Preferred protecting groups are trityls, particularly monomethoxytrityl and dimethoxytrityl. Most preferred is dimethoxytrityl (DMT).

Bifunctional silylating reagents contemplated by the present invention have the formula:

where each R is independently $C_1$–$C_6$ alkyl; and $R^1$ is a leaving group. In a preferred embodiment, the silylating reagent is symmetrical and R is isopropyl or methyl and $R^1$ is Cl or $SO_2CF_3$.

The alkaline aprotic solution preferably comprises a proton acceptor, such as a base, dissolved in an aprotic solvent. Suitable bases and solvents are known and readily apparent to those of skill in the art. A preferred base is a hindered base exemplified by 2,6-di-tert-butyl-4-methylpyridine. A preferred solvent is a mixture of dimethylformamide (DMF) and acetonitrile ($CH_3CN$).

Nucleosides utilized with the present invention include both oxy- and deoxy-nucleotides. The purine and pyrimidine moieties of such nucleosides are optionally protected at exocyclic amino groups. A preferred protecting group for the exocyclic amino groups of adenine and cytosine is the benzoyl moiety. A preferred protecting group for the exocyclic amino group of guanine is the isobutyl moiety. Optionally, guanine may also be protected at the $O^6$ position.

The 3'-silylated nucleoside used in the method of the present invention may be a nucleoside monomer or the 3'- terminal nucleoside of an oligonucleotide or oligonucleotide analog. The 3',5'- unprotected nucleoside used in the method of the present invention may be a nucleoside monomer or the 5'- terminal nucleoside of an oligonucleotide or oligonucleotide analog in which both the 3'- and 5'- terminal nucleosides are unprotected. The oligonucleotide analog can have any type of internucleoside linkage.

Alternatively, the method of the present invention is employed to synthesize oligonucleotide analogs having only siloxane internucleoside linkages. Synthesis of such oligonucleotide analogs proceeds in accordance with modified solution phase or solid phase synthetic processes, Gait, supra.

In a preferred solution phase method, the reaction of a monomeric 3'-silylated-5'-protected nucleoside with a first monomeric unprotected nucleoside is followed by reaction of the 5'-protected silyl linked (3' to 5') dinucleoside product (nucleoside dimer) with a bifunctional silylating reagent and a second unprotected monomeric nucleoside to form a 5'-protected, silyl linked trimer (trinucleoside). The length of the chain is extended by repeating these reaction steps until an oligonucleotide analog (nucleoside polymer) of desired length is achieved.

Alternatively, and preferably, chain extension or elongation proceeds by isolating the 5'-protected, silyl linked polymers as they are formed, removing the 5'-protecting group and using such unprotected nucleoside polymers in place of the unprotected monomeric nucleosides. In this way, chain elongation proceeds in a more rapid and efficient stoichiometric manner (i.e. trimer+dimer, trimer+trimer).

In a preferred embodiment, oligonucleotide analogs having siloxane internucleoside linkages are synthesized by a modified solid phase synthetic process employing the linking method of the present invention.

The initial step in solid phase synthesis is attachment of a 5'-protected nucleoside to a solid support, preferably a controlled pore glass (CPG) support. The nucleoside is preferably attached to the CPG support via a succinate linkage at the 3'-hydroxyl position of the nucleoside. Other means of attaching nucleosides to solid supports are known and readily apparent to those of skill in the oligonucleotide synthesis art. Also, such 5'-protected nucleosides linked to a CPG support are commercially available.

Following attachment of the first nucleoside to the solid support, chain elongation occurs via the sequential steps of removing the 5'-hydroxyl protecting group from the attached nucleoside, adding a 5'-protected-3'-silylated nucleoside together with an activating reagent, and capping the unreacted chains.

The protecting group at the 5'-hydroxyl position of the attached nucleosides is removed with acid, preferably trichloroacetic acid.

The activation step occurs in the presence of an added silylated nucleoside and a hindered base activating reagent. A preferred activating reagent is a hindered base such as, 2,6-di-tert-butyl-4-methylpyridine. A preferred solvent is a mixture of acetonitrile and DMF. Unreacted chains are terminated or capped with capping reagents such as acetic anhydride and N-methyl imidazole.

After the desired oligonucleotide chain assembly is complete, the chains are separated from the solid support and the protecting groups are removed by conventional methods. Gaits, supra at pp 67-70.

Preferably, completed chains are cleaved from the solid support by a solution of aqueous ammonia in isopropanol and acetonitrile.

Using the solid phase synthetic procedures set forth above, 3',5'-silyl linked nucleoside polymers or oligonucleotide analogs having siloxane internucleoside linkages of any desired length can be prepared.

Those skilled in the art will appreciate that other means of synthesizing oligonucleotides can be modified in an analogous manner to produce oligonucleotide analogs having siloxane internucleoside linkages. Similarly, those skilled in the art will appreciate that the methods of the present invention can be used in conjunction with known methods of preparing oligonucleotides or analogs thereof having other types of internucleoside linkages to prepare oligonucleotide analogs having mixtures of siloxane and such other linkages.

The method of the present invention can be utilized to synthesize a variety of oligonucleoside sequences comprising bases which, when substituted for the naturally occurring bases in DNA and RNA, enable oligonucleotide analogs in which they are incorporated to hybridize with target segments of DNA or RNA. Suitable bases include adenine (A), cytidine (C), guanine (G), uracil (U), thymine (T) and modifications thereof, as for example, 5-bromo or 5-iodouracil, 5-methyl cytosine, isocytosine (2-amino-4-oxopyrimidine), isoguanine (2-oxo-6-amino purine), Inosine (6-oxo purine), 5-vinyl uracil and 5-vinylcytosine.

The following examples further illustrate the invention and are not to be construed as limiting of the specification and claims in any way.

EXAMPLE 1

Synthesis of
5'-O-dimethoxytrityl-3'-O-(5'-dimethylsilyl-3'-O-acetyl-thymidyl) thymidine A solution of 5'-O-dimethoxytrityl thymidine (7.35 mmol, 4.0 g) in $CH_2Cl_2$(40 ml) and triethylamine (16.16 mmol, 2.2 ml) was slowly cannulated into a solution of dichlorodimethylsilane (7.35 mmol, 0.948 g, 0.89 ml) in $CH_2Cl_2$ (100 ml) at $-40°$ C. (dry ice-$CH_3CN$) and stirred at $-40°$ C. for 3 hours. A solution of 3'-O-acetyl-thymidine (3.5 mmol, 1.0 g) and triethylamine (16.16 mmol, 2.2 ml) in $CH_2Cl_2$ (25 ml) was added and the reaction was stirred at 0° C. for 3 hours. The reaction was quenched by adding 5% aqueous $NaHCO_3$ (25 ml). The organic layer was washed with brine (2×25 ml) and dried over $Na_2SO_4$. Crude product (5.3 g) was purified by column chromatography ($SiO_2$, gradient of ethyl acetate/hexanes).

Isolated yield: 670 mg, 22%. Rf 0.23(7:3 EtOAc:Hexanes). $^1$H NMR (300 MHz, $CDCl_3$) δ 9.02 (s, 1 H, NH), 8.95 (s, 1 H, NH), 7.64 (s, 1 H), 7.50 (s, 1 H), 7.41-7.27 (m, 9 H), 6.84 (d, J=7.7 Hz, 4 H), 6.38 (m, 2 H), 5.19 (d, J=5.6 Hz, 1 H), 4.61 (d, J=2.5 Hz, 1 H), 4.04 (s, 2 H), 3.87 (s, 2 H), 3.79 (s, 6 H), 3.39 (ABq, J=10.4 Hz, Δν=67.3 Hz, 2 H), 2.41-2.26 (m, 4 H), 2.09 (s, 3 H), 1.89 (s, 3 H), 1.50 (s, 3 H), 0.16 (s, 3 H), 0.15 (s, 3 H). FABMS (TG/G, 5% HOAc): $(M+H)^+ = 884.6$.

EXAMPLE 2

Synthesis of
5'-O-dimethoxytrityl-3'-O-(5'-O-diisopropylsilylthymidyl) thymidine Method A. (Hindered base catalyst) A solution of 5'-O-dimethoxytritylthymidine (0.92 mmol, 0.5 g) and 2,6-di-tert-butyl-4-methylpyridine (0.23 mmol, 47 mg) in DMF (4 ml) was added to a solution of 2,6-di-tert-butyl-4-methylpyridine (1.0 mmol, 0.2 g) and diisopropylsilylbistriflate (1.0 mmol, 0.30 ml) in CH₃CN (5 ml) at −40° C. After 30 min at −40° C., the reaction was allowed to warm to room temperature. Imidazole (1.0 mmol, 70 mg) was added, followed by the addition of unprotected thymidine (0.8 mmol, 193 mg). The reaction was stirred for 1 hour and then added dropwise to a vigorously stirred icewater mixture (500 ml). The resulting mixture was then stirred for 30 min. and filtered. Crude product was chromatographically purified.

Isolated yield 70%. Rf 0.45 (5% MeOH/EtOAc). $^1$H NMR (300 MHz, CDCl$_3$) δ 9.85 (s, 1 H, NH), 9.44 (s, 1 H, NH), 7.64 (s, 1 H), 7.41–7.24 (m, 10 H), 6.84 (d, J=7.8 Hz, 4 H), 6.33 (m, 2 H), 4.65 (s, 1 H), 4.43 (d, J=2.2 Hz, 1 H), 4.11 (d, J=2.56, 1 H), 4.00 (d, J=3.36, 1 H), 3.93 (ABq, J=3.7 Hz, 11.0 Hz, Δν=24.6, 2 H), 3.79 (s, 6 H), 3.39 (ABq, J=3.0 Hz, 10.8 Hz, Δν=49.5 Hz, 2 H), 2.50–2.38 (m, 2 H), 2.30–2.07 (m, 2 H), 1.88 (s, 3 H), 1.56 (s, 3 H), 1.05–0.98 (m, 14 H). $^{13}$C NMR (CDCl$_3$) δ 164.84, 164.80. 159.40, 151.72, 151.25, 144.89, 136.16, 136.01, 135.86, 130.60, 128.58, 127.75, 113.80, 112.10, 111.42, 87.48, 87.38, 85.76, 85.48, 73.90, 71.70, 63.82, 63.48, 60.75, 55.57, 41.71, 40.85, 21.24, 17.52, 17.47, 17.39, 14.35, 12.69, 12.18, 12.10, 11.85. FABMS (TG/G): (M+H)$^+$ =899.

Anal. Calcd for C$_{47}$H$_{58}$N$_4$O$_{12}$Si: C, 62.79; H, 6.50; N, 6.23; MW, 898. Found: C, 61.83; H, 6.53; N, 6.23.

Method B. (Unhindered base catalyst) A solution of 5'-O-dimethoxytritylthymidine (6.65 mmol, 3.54 g) and imidazole (13.3 mmol, 0.88 g) in DMF (18 ml) was added slowly via a dropping funnel to a solution of dichlorodiisopropylsilane (6.62 mmol, 1.22 g, 1.20 ml) in DMF (4.5 ml) at −40° C. (dry ice-CH$_3$CN). The reaction was stirred at −40° C. for 1 hour. A solution of unprotected thymidine (6.65 mmol, 1.61 g) and imidazole (1.33 mmol, 0.9 g) in DMF (15 ml) was added via a dropping funnel. The reaction was stirred at −40° C. for 1 hour then warmed to room temperature overnight. The reaction mixture was then added dropwise to a vigorously stirred ice-water mixture (1 L) and stirred for 30 min. The mixture was filtered to yield the product as a white solid which was air dried and subjected to column chromatography (SiO$_2$, gradient of 60% to 100% EtOAc/hexanes). Isolated yield: 1.47 g, 25%.

EXAMPLE 3

Synthesis of
N$^6$-benzoyl-2'-deoxy-5'-O-dimethoxytrityl-3'-O-(5'-diisopropylsilylthymidyl) adenosine N$^6$-Benzoyl-2'-deoxy-5'-O-dimethoxytrityladenosine (5 mmol, 3.28 g) and imidazole (10 mmol, 0.68 g) were dissolved in DMF (15 ml) and added slowly via a dropping funnel to a solution of dichlorodiisopropylsilane (5 mmol, 0.9 ml) in DMF (1.5 ml) at −40° C. (dry ice-CH$_3$CN). The reaction was stirred at −40° C. for 1 hour and a solution of thymidine (7.5 mmol, 1.81 g) and imidazole (7.5 mmol, 0.51 g) in DMF (20 ml) was added via a dropping funnel. The reaction was stirred at −40° C. for 1 hour and then warmed to room temperature overnight. The reaction mixture was then added dropwise to a vigorously stirred ice-water mixture (1 L) and stirred for 30 min. The precipitate was filtered and dried to give a white solid (5.8 g), which was purified by preparative TLC (1 mm SiO$_2$, 3% MeOH/EtOAc).

Isolated yield: 50 mg, 38%. Rf 0.32 (2% MeOH/EtOAc). $^1$H NMR (300 MHz, CDCl$_3$) δ 9.99 (s, 1 H, NH), 8.76 (s, 1 H), 8.22 (s, 1 H), 8.09 (d, J=7.8, 2 H), 7.55–7.13 (m, 13 H), 6.74 (m, 4 H), 6.42 (t, J=5.8 Hz, 1 H), 6.25 (t, J=6.0, 1 H), 4.96 (d, J=5.4 Hz, 1 H), 4.48 (s, 1 H), 4.19 (d, J=3.8 Hz, 1 H), 3.94 (s, 1 H), 3.83–3.72 (m, 2 H), 3.72 (s, 6 H), 3.38 (d, J=3.4 Hz, 2 H), 2.83–2.76 (m, 1 H), 2.60–2.52 (m, 1 H), 2.45–2.38 (m, 1 H), 2.05–1.95 (m, 1 H), 1.79 (s, 3 H), 0.95 (m, 14 H). FABMS (TG/G): (M—H)$^-$ =1011.

EXAMPLE 4

Synthesis of
N$^4$-benzoyl-2'-deoxy-5'-O-dimethoxytrityl-3'-O-(5'-O-diisopropylsilylthymidyl) cytidine The procedure described above in Example 3 was employed for the synthesis of the title compound. Purification by preparative TLC (1 mm SiO$_2$, 3% MeOH/EtOAc) gave pure product.

Estimated yield: 70%. Rf 0.40 (2% MeOH/EtOAc). $^1$H NMR (CDCl$_3$) δ 9.54 (s, 1 H, NH), 8.21 (d, J=7.6 Hz, 1 H), 7.94 (d, J=8.2 Hz, 2 H), 7.59–7.24 (m, 14 H), 6.83 (d, J=8.4 Hz, 4 H), 6.25 (m, 2 H), 4.58 (s, 1 H), 4.46 (s, 1 H), 4.17 (s, 1 H), 4.07–3.80 (m, 3 H), 3.77 (s, 6 H), 3.39 (ABq, J=3.0 Hz, 10.9 Hz, Δν=29.1, 2 H), 2.84–2.78 (m, 1 H), 2.46–2.41 (m, 1 H), 2.14–1.79 (m, 2 H), 1.84 (s, 3 H), 0.98 (m, 14 H). FABMS (NBA): (M—H)$^-$ =987.

EXAMPLE 5

Synthesis of
3'-Silylated-N$^4$-benzoyl-2'-deoxy-5'-O-dimethoxytritylcytidine

Method A. A solution of N$^4$-benzoyl-2'-deoxy-5'-O-dimethoxytritylcytidine (0.4 mmol, 260 mg) and imidazole (0.8 mmol, 52 mg) in CH$_3$CN (1.6 ml) was slowly added via a syringe to a solution of dichlorodiisopropylsilane (0.4 mmol, 72 μl) in CH$_3$CN (0.4 ml) at −40° C. (dry ice-CH$_3$CN). The reaction mixture was allowed to stir at −40° C. for 30 min, then at room temperature for 30 min. The reaction mixture was filtered, and the product (3'-O-silylated cytidine) isolated by column chromatography (SiO$_2$, gradient of 60% EtOAc/Hex to 100% EtOAc to 1% MeOH/EtOAc).

Yield: 100 mg, 28%. Rf 0.71 (0.5% MeOH/EtOAc). Also isolated was 50 mg of a 3'—3' symmetrical C—C dimer. $^1$H NMR (300 MHz, CDCl$_3$) δ 8.43 (d, J—7.6 Hz, 1 H), 7.88 (d, J=8.2 Hz, 2 H), 7.60–7.26 (m, 13 H), 6.87 (d, J=8.4 Hz, 4 H), 6.25 (t, J=6.5 Hz, 1 H), 4.71 (m, 1 H), 4.10 (m, 1 H), 3.80 (s, 6 H), 3.48 (ABq, J=3 Hz, 11 Hz, Δν30 Hz, 2 H), 2.67 (m, 1 H), 2.35 (m, 1 H), 0.97 (m, 14 H). FABMS (TG/G): (M+H)$^+$ =884.6.

Method B. To minimize formation of the 3',3' symmetrical dimer, a solution of N$^4$-benzoyl-2'-deoxy-5'-O-dimethoxytritylcytidine (3.08 mmol, 2.0 g) in DMF/CH$_3$CN (5 ml/2 ml) was added dropwise at −40° C. (dry ice-CH$_3$CN) to a solution of diisopropylsilylbistriflate (3.38 mmol, 1.0 ml) and 2,6-di-tert-butyl-4-methylpyridine (3.38 mmol, 700 mg) in CH$_3$CN (8 ml). The reaction mixture was stirred at −40° C. for 30 min. and the product purified by TLC.

EXAMPLE 6

Detritylation of 5'-O-dimethoxytrityl-3'-O-(5'-O'-diisopropylsilylthymidyl) thymidine A solution of the title compound (22 mmol, 200 mg) in CH$_2$Cl$_2$ (4 ml) was added to 3% trichloroacetic acid in CH$_2$Cl$_2$ (6 ml). The bright orange solution was stirred at room temperature for 10 min. The reaction mixture was poured into 5% aqueous NaHCO$_3$ (5 ml) and extracted into 5% MeOH/EtOAc. The organic layer was washed with brine (10 ml) and dried over Na$_2$SO$_4$. Crude product was purified by column chromatography (SiO$_2$, gradient of 60:40 EtOAc/Hex to 10% MeOH/EtOAc).

Isolated yield: 90 mg, 70%. Rf 0.40 (10% MeOH/EtOAc). $^1$H NMR (300 MHz, CD$_3$OD) δ 7.54 (s, 1 H), 7.28 (s, 1 H), 6.03 (m, 2 H), 4.46 (m, 1 H), 4.18 (m, 1 H), 3.82–3.69 (m, 3 H), 3.50 (m, 4 H), 2.06–1.97 (m, 4 H), 1.62 (s, 6 H), 0.85 (m, 14 H). FABMS (TG/G): (M+H)$^+$ = 597.3.

EXAMPLE 7

Synthesis of 5'-O-dimethoxytrityl-3'-O-[5'-O-diisopropylsilylthymidyl-3'-O-(5'-O-diisopropylsilylthymidyl)] thymidine
Chem. Abstr. Index name is Thymidine, 5'-O-[bis(1-methylethyl)silylene]-5'-O-dephosphinicothymidyly-(5'.fwdarw.3')-5'-O-[bis(1-methylethyl)silylene]-5'-O-dephosphinicothymidylyl-(5'.fwdarw.3')-5'-O-[bis(4-methoxyphenyl)phenylmethyl]-

Method A. A solution of 5'-O-dimethoxytritylthymidine (14.7 mmol, 8.0 g) and imidazole (29.94 mmol, 2.0 g) in DMF (40 ml) was added slowly via a dropping funnel to a solution of dichlorodiisopropylsilane (14.7 mmol, 2.72 g, 2.64 ml) in DMF (10 ml) at −40° C. (dry ice-CH$_3$CN). The reaction was stirred at −40° C. for 1 hour. A solution of thymidine (14.7 mmol, 3.56 g) and imidazole (29.4 mmol, 2.0 g) in DMF (40 ml) was added via a dropping funnel. The reaction was stirred at −40° C. for 1 hour then reaction cannulated under N$_2$ to a solution of dichlorodiisopropylsilane (14.7 mmol, 2.72 g, 2.64 ml) in DMF (10 ml) at −40° C. The reaction mixture was stirred at −40° C. for 1 hour. A solution of thymidine (14.7 mmol, 3.56 g) and imidazole (29.4 mmol, 2.0 g) in DMF (40 ml) was added and the reaction was stirred at −40° C. for 1 hour. The resulting mixture was added dropwise to a vigorously-stirred ice/water mixture (2 L) and stirred for 30 min. The precipitate was filtered and air-dried. The white solid (27 g) was subjected to column chromatography (150 g SiO$_2$, gradient of 60% to 100% EtOAc/hexanes) to give pure product. Isolated yield: 1.8 g, 10%.

Method B. A solution of 5'-O-dimethoxyltrityl-3'-O-(5'-O-diisopropylsilylthymidyl) thymidine (1.11 mmol, 1.0 g) and 2,6-di-tert-butyl-4-methylpyridine (0.28 mmol, 60 mg) in DMF (3 ml) was added via a syringe to a solution of diisopropylsilylbistriflate (1.22 mmol, 0.504 g, 0.360 ml) and 2,6-di-tert-butyl-4-methylpyridine (1.22 mmol, 0.25 g) in CH$_3$CN (3 ml) at −40° C. (dry ice-CH$_3$CN). The reaction was stirred for 1 hour at −40° C. A solution of imidazole (1.22 mmol, 0.16 g) in CH$_3$CN (2.5 ml) was added and the reaction warmed to room temperature. A solution of thymidine (1.11 mmol, 0.269 g) in DMF (2 ml) was added and the reaction stirred for 1 hour and then added dropwise to a vigorously-stirred ice/water mixture (1 L) and stirred for an additional 30 min. The precipitate was filtered and air-dried to give a white solid (1.5 g), which was triturated with hexanes (20 ml) to give pure product.

Isolated yield: 1.05 g, 76%. Rf 0.38 (5% MeOH/EtOAc). $^1$H NMR (300 MHz, CDCl$_3$) δ 7.62 (s, 1 H), 7.36–7.22 (m, 11 H), 6.80 (d, J=7.7, 4 H), 6.36–6.22 (m, 3 H), 4.62–4.54 (m, 2 H), 4.45 (m, 1 H), 4.06–3.83 (m, 7 H), 3.75 (s, 6 H), 3.36 (ABq, J=10.0 Hz, Δν=47.6 Hz, 2 H), 2.45–2.30 (m, 3 H), 2.28–2.14 (m, 1 H), 2.13–2.00 (m, 2 H), 1.85 (s, 3 H), 1.81 (s, 3 H), 1.48 (s, 3 H), 0.98 (m, 28 H). $^{13}$C NMR (CDCl$_3$) δ 164.54, 164.45, 164.33, 159.00, 151.12, 150.99, 144.40, 135.73, 135.51, 135.40, 130.15, 128.16, 113.37, 111.54, 111.32, 111.07, 87.50, 87.02, 85.23, 85.02, 73.35, 72.98, 71.24, 63.28, 63.02, 55.15, 41.33, 40.64, 40.25, 17.04, 17.00, 16.92, 12.26, 11.70, 11.59, 11.53, 11.47. FABMS (TG/G): (M+H)$^+$ = 1252.5.

Anal Calcd. for C$_{63}$H$_{84}$N$_6$O$_{17}$Si$_2$: C, 60.38; H, 6.71; N, 6.71; MW, 1253.6. Found: C, 60.44; H, 6.84; N, 6.56.

EXAMPLE 8

Detritylation of 5'-O-dimethoxytrityl trimer

A solution of 5'-O-dimethoxytrityl trimer (0.638 mmol, 0.80 g) in CH$_2$Cl$_2$ (12 ml) was added to 3% (v/v) trichloroacetic acid/CH$_2$Cl$_2$ (14 ml). The bright orange solution was stirred at room temperature for 1 hour and then poured into 5% aqueous NaHCO$_3$ (15 ml) and extracted into 5% MeOH/EtOAc. The organic layer was washed with brine (20 ml) and dried over Na$_2$SO$_4$. The product was purified by column chromatography (SiO$_2$, gradient of EtOAc/MeOH 100% to 95%).

Isolated yield: 420 mg, 70%. Rf 0.50 (10% MeOH/EtOAc). $^1$H NMR (300 MHz, CD$_3$OD) δ 7.55 (s, 1 H), 7.27 (m, 2 H), 6.05 (m, 3 H), 4.47 (m, 2 H), 4.16 (m, 1 H), 3.87–3.70 (m, 7 H), 3.50 (m, 2 H), 2.14–1.96 (m, 6 H), 1.62 (s, 9 H), 0.92 (m, 28 H). FABMS (TG/G): (M−H)$^-$ = 950.

EXAMPLE 9

Synthesis of 5'-O-dimethoxytrityl-3'-O-[5'-O-diisopropylsilylthymidyl-3'-O-{(5'-O-diisopropylsilylthymidyl)-3'-O-(5'-O-diisopropylsilylthymidyl)}] thymidine (Tetranucleotide Analog)

A solution of 5'-O-dimethoxytrityl trimer (20 μmol, 25 mg) and 2,6-di-tert-butyl-4-methylpyridine (40 μmol, 8.25 mg) in DMF (200 μl) was added slowly via a syringe to a solution of diisopropylsilylbistriflate (20 μmol, 6 μl) and 2,6-di-tert-butyl-4-methylpyridine (20 μmol, 4.1 mg) in DMF (100 μl) in a 5 ml round bottom flask cooled to −40° C. (dry ice-CH$_3$CN). The reaction was stirred for 1 hour and a solution of thymidine (20 μmol, 4.84 mg) and imidazole (40 μmol, 2.7 mg) in DMF (200 μl) was then added. Stirring continued at −40° C. for 30 min. The reaction was warmed to room temperature. Aqueous NaHCO$_3$ (1 ml of a 5% solution) was added and the reaction mixture extracted into CHCl$_3$ (2×5 ml), washed with brine (1 ml) and dried over Na$_2$SO$_4$. Product was purified by preparative reverse-phase HPLC [Ultrasphere ODS, 20% 0.01M triethylammonium acetate pH 7.5, 80% CH$_3$CN].

Isolated yield: 10 mg, 31%. Rf 0.16 (5% MeOH/EtOAc). $^1$H NMR (300 MHz, CDCl$_3$) δ 7.65 (s, 1 H), 7.39–7.26 (m, 12 H), 6.85 (d, J=7.7 Hz, 4 H), 6.38–6.27 (m, 4 H), 4.66–4.45 (m, 4 H), 4.10–3.85 (m, 10 H), 3.80 (s, 6 H), 3.39 (ABq, J=11 Hz, Δν=45 Hz, 2 H), 2.45–2.08 (m, 8 H), 1.92 (s, 3 H), 1.90 (s, 3 H), 1.87 (s, 3 H), 1.56

(s, 3 H), 1.03 (m, 42 H). FABMS (TG/G): $(M+H)^+ = 1608.3$; $(M+Na)^+ = 1630.0$.

EXAMPLE 10

Synthesis of pentathymidyl nucleotide analog with silyl linkages

A solution of 5'-dimethoxytrityl trimer (58.4 μmol, 73 mg) and 2,6-di-tert-butyl-4-methylpyridine (29.2 μmol, 6 mg) in DMF (600 μl) was added slowly via a syringe to a solution of diisopropylsilylbistriflate (58.4 μmol, 17.5 μl) and 2,6-di-tert-butyl-4-methylpyridine (58.4 μmol, 12 mg) in DMF (300 μl) in a 5 ml round bottom flask cooled to $-40°$ C. (dry ice-CH$_3$CN). The reaction was stirred for 1 hour and a solution of the detritylated dimer (55.5 μmol, 50.6 mg) and imidazole (100 μmol, 6.75 mg) in DMF (300 μl) was added. The reaction was stirred for 1 hour at $-40°$ C., then warmed to room temperature. Aqueous NaHCO$_3$ (2 ml of a 5% solution) was added and the mixture was extracted into CHCl$_3$ (2×10 ml), washed with brine (2 ml) and dried over Na$_2$SO$_4$ to yield product.

FABMS (TG/G): $(M+H)^+ = 1961$. Fragment ions at 1900, 1607, 1252, 898 and 544. FABMS (NBA): $(M-H)^- = 1961$.

EXAMPLE 11

Solid-phase synthesis of thymidine decanucleotide

A. Synthesis of the monomeric synthetic unit. Diisopropylsilylbistriflate (2 mmol, 0.60 ml) was added via a syringe to a solution of 2,6-di-tert-butyl-4-methylpyridine (2 mmol, 0.41 g) in CH$_3$CN (5 ml) in a 100 ml round bottom flask under N$_2$. The clear solution was cooled to $-40°$ C. (dry ice-CH$_3$CN) and a solution of 5'-O-dimethoxytritylthymidine (1.84 mmol, 1.0 g) and 2,6-di-tert-butyl-4-methylpyridine (0.46 mmol, 94 mg) in DMF (5 ml) was added dropwise via a syringe over 10 min. The reaction was stirred at $-40°$ C. for 1 hour. A solution of imidazole (3.7 mmol, 250 mg) in DMF (4 ml) was added, followed by dilution with CH$_3$CN (5 ml) to a final concentration of 0.1M. B. Synthesis of the decanucleotide. The mixture was warmed to room temperature and employed in a solid-phase automated synthesis of the decanucleotide.

$^1$H NMR (300 MHz, CD$_3$OH) δ 7.55–7.47 (m, 10 H), 6.23–6.33 (m, 10 H), 4.69 (s, br, 9 H), 4.40 (s, br, 1 H), 4.10–3.40 (m, 19 H), 3.25–3.08 (m, 1 H), 2.55–2.20 (m, 20 H), 1.87 (s, br, 27 H), 1.30 (s, br, 3 H), 1.08 (m, 126 H). FABMS (TG/G): $(M-H)^- = 3434.2$; $(M+H)^+ = 3433.7$. FABMS (NBA): $(M-H)^- = 3435.2$. M.F. C$_{154}$H$_{248}$N$_{20}$O$_{50}$; Sig. Calc: MW, 3432.5.

EXAMPLE 12

Synthesis of 5'-O-dimethoxytrityl-3'-O-(5'-O-dimethoxytrityl-3'-O-(5'-O-diisopropylsilylthymidyl)thymidine 3'-N,N-diisopropyl(2-cyanoethyl)phosphoramidite 5'-O-dimethoxytrityl dimer (0.1 mmol, 90 mg) was coevaporated from tetrahydrofuran/pyridine (6 ml) (ratio 2:1) twice, dissolved in THF (500 μl) and added dropwise via a syringe to a stirred solution of 4-dimethylaminopyridine (4 mg), diisopropylethylamine (distilled from CaH$_2$, 0.4 mmol, 87 μl) and 2-cyanoethyl-N,N-diisopropylchlorophosphoramidite (0.15 mmol, 28.77 μl) in THF (500 μl) under N$_2$ flow at room temperature. The reaction was stirred for 2 hour. To remove trace amounts of 5'-O-dimethoxytrityl-3'-O -(5'-O-diisopropylsilylthymidyl)thymidine, additional 2-cyanoethyl-N,N-diisopropylchlorophosphoramidite (0.025 mmol, 5 μl) was added. The reaction was stirred 1 hour and added to EtOAc (10 ml, pre-washed with 5 ml brine), washed with brine (2×2 ml) and dried over Na$_2$SO$_4$. Crude product was purified by column chromatography (SiO$_2$, 1:1 EtOAc/hexanes).

Isolated yield: 82 mg, 74.5%. Rf 0.70 (1% MeOH-/EtOAc). $^1$H NMR (300 MHz, CDCl$_3$) δ 8.96 (s, br, 1 H, NH), 7.64 (s, 1 H), 7.40–7.22 (m, 10 H), 6.84 (d, J=8.8, 4 H), 6.40 (t, J=6.5 Hz, 1 H), 6.27 (t, J=6.5 Hz, 1 H), 4.67 (m, 1 H), 4.53 (m, 1 H), 4.10 (m, 2 H), 3.93 (m, 1 H), 3.87 (m, 1 H), 3.80 (s, 6 H), 3.61 (m, 2 H), 3.39 (ABq, J=4 Hz, 10 Hz, Δν=42 Hz, 2 H), 2.64 (m, 2 H), 2.53–2.05 (m, 4 H), 1.86 (s, 3 H), 1.51 (s, 3 H), 1.26 (m, 2 H), 1.17 (m, 12 H), 1.01 (m, 14 H). $^{13}$C NMR (CDCl$_3$) δ 163.58, 163.44, 158.72, 150.14, 144.18, 135.47, 135.25, 129.99, 127.99, 127.16, 117.58, 113.26, 111.16, 111.02, 110.94, 86.96, 86.23, 85.82, 85.74, 84.90, 84.74, 84.64, 73.41, 73.22, 63.40, 62.89, 62.70, 58.25, 58.17, 57.98, 57.87, 55.23, 43.36, 43.17, 41.47, 39.69, 39.47, 24.52, 24.44, 22.96, 20.42, 20.32, 17.24, 17.05, 12.44, 11.92, 11.71, 11.57. $^{31}$P NMR (CDCl$_3$, referenced to H$_3$PO$_4$) δ 149.16; IR (KBr) 3192, 3058, 2965, 2932, 2868, 2838, 2246, 1693, 1608, 1510, 1465, 1398, 1382, 1365, 1322, 1289, 1274, 1251, 1199, 1179, 1158, 1129, 1084, 1064, 1035, 1003, 978, 913, 885, 828, 812, 794, 773, 756, 727, 702 cm$^{-1}$. FABMS (NBA): $(M+H)^+ = 1099$.

Anal. Calcd. for C$_{56}$H$_{75}$N$_6$O$_{13}$PSi: C, 61.19; H, 6.88; N, 7.64; MW, 1100. Found: C, 60.60; H, 6.87; N, 7.60.

EXAMPLE 13

Synthesis of 5'-O-dimethoxytrityl-3'-O-[5'-O-diisopropylsilylthymidyl-3'-O (5'-O-diisopropylsilylthymidyl)]thymidine-3'-N,N-diisopropyl(2-cyanoethyl)-phosohoramidite (Trimer)

5'-Dimethoxytrityl-trimer (0.44 mmol, 550 mg) was coevaporated from THF (20 ml)/pyr (10 ml) twice, dissolved in CH$_2$Cl$_2$ (2 ml) and added dropwise via a syringe to a stirred solution of 4-dimethylaminopyridine (20 mg), diisopropylethylamine (distilled from CaH$_2$; 1.69 mmol, 370 μl) and 2-cyanoethyl N,N-diisopropyl-chlorophosphoramidite (0.64 mmol, 120 μl) in CH$_2$Cl$_2$ (2.0 ml) under N$_2$ flow at 0° C. The reaction mixture was then brought to room temperature, stirred for 1 hour, poured into EtOAc (prewashed with 25 ml brine; 50 ml), washed with brine (2×20 ml) and dried over Na$_2$SO$_4$. Crude product was purified by column chromatography (10 g SiO$_2$, EtOAc).

Isolated yield: 320 mg, 64%. Rf 0.76 (EtOAc). $^1$H NMR (300 MHz, CDCl$_3$) δ 7.63 (s, 1 H), 7.41–7.22 (m, 11 H), 6.83 (d, J=7.8 Hz, 4 H), 6.40–6.24 (m, 3 H), 4.67–4.54 (m, 3 H), 4.13–3.85 (m, 7 H), 3.75 (s, 6 H), 3.55 (m, 2 H), 3.48–3.28 (m, 2 H), 2.74 (t, J=6 Hz, 2 H) 2.45–2.03 (m, 6 H), 1.88 (s, 3 H), 1.83 (s, 3 H), 1.50 (s, 3 H), 1.28–1.13 (m, 14 H), 1.00 (m, 28 H). FABMS (NBA): $(M-H)^- = 1453$.

EXAMPLE 14

Synthesis of 5'-O-dimethoxytrityl-3'-O-(3'-O-diisopropylsilyl-5'-O-dimethoxytritylthymidyl) thymidine (3',3'-dimer)

In the preparation of a 3',5' thymidinethymidine dimer, using the silylation procedure described in Example 13, a 3',3'-dimer was observed as a major by-product. The title compound was isolated from crude reaction product (800 mg) by column chromatography (SiO$_2$, gradient of 60% to 90% EtOAc/hexanes).

Rf 0.41 (60% ETOAc/Hex). $^1$H NMR (300 MHz, CDCl$_3$) δ 9.95 (s, br, 1 H, NH), 8.63 (s, br, 1 H, NH), 7.51 (s, 2 H), 7.35–7.15 (m, 18 H), 6.77 (d, J=8.7 Hz, 8 H), 6.34 (m, 2 H), 4.57 (d, J=4.3 Hz, 2 H), 3.91 (s, 2 H), 3.71 (s, 12 H), 3.24 (ABq, J=2.8 HZ, 10.7 Hz, Δν=54 Hz, 4 H), 2.46 (m, 2 H), 2.26 (m, 2 H), 1.46 (s, 6 H), 0.88 (m, 14 H). FABMS (NBA): (M—H)$^-$ =1200.1.

EXAMPLE 15

Synthesis of N$^6$-benzoyl-2'-deoxy-5'-O-dimethoxytrityl-3'-O-(3'-O-diisopropylsilyl-N$^6$-benzoyl-2'-deoxy-5'-O-dimethoxytrityladenosyl)adenosine In the preparation of the 3',5' adenosine-thymidine dimer, a 3',3' dimer was observed as a major byproduct of the silylation step. A portion of this crude product (100 mg) was purified by preparative TLC (1 mm SiO$_2$, 3% MeOH/EtOAc) to give pure material.

Rf 0.45 (90% EtOAc/hexanes). $^1$H NMR (300 MHz, CDCl$_3$) δ 8.60 (s, 2 H), 8.14 (s, 2 H), 8.00 (d, J=8 Hz, 2 H), 7.62 (s, 2 H), 7.57–7.04 (m, 22 H), 6.73 (d, J=9, 8 H), 6.38 (m, 2 H), 4.79 (m, 2 H), 4.14 (m, 2 H), 3.68 (s, 12 H), 3.52–3.24 (m, 4 H), 2.86 (m, 2 H), 2.51 (m, 2 H), 0.98 (m, 14 H). FABMS (NBA): (M+H)$^+$ =1428.3, (M—H)$^-$ =1426.4.

EXAMPLE 16

Synthesis of N$^4$-benzoyl-2'deoxy-5'-O-dimethoxytrityl-3'-O-(3'-O-diisopropylsilyl-N$^4$-benzoyl-2'-deoxy-5'-O-dimethoxytritylcytidyl)cytidine.

In the silylation of N$^4$-benzoyl-2'-deoxy-5'-O-dimethoxytritylcytidine, using the procedure described by Example 15, a 3',3' dimer was observed as a major byproduct. This dimer was a isolated from crude reaction mixture by column chromatography (SiO$_2$, gradient of 60% to 100% EtOAc/Hex to 1% EtOAc/MeOH) to yield the title compound.

Rf 0.31 (1% MeOH/EtOAc). $^1$H NMR (300 MHz, CDCl$_3$) δ 8.82 (s, br, 1 H, NH), 8.28 (d, J=8 Hz, 1 H), 8.25 (d, J=8 Hz, 1 H), 7.89 (m, 4 H), 7.63-7.24 (m, 26 H), 6.85 (m, 8 H), 6.23 (m, 2 H), 4.57 (m, 2 H), 4.20 (m, 2 H), 3.80 (s, 12 H), 3.50–3.23 (m, 4 H), 2.60 (m, 2 H), 2.15 (m, 2 H), 0.96 (m, 14 H). FABMS (NBA): (M+H)$^+$ =1379.2, (M—H)$^-$ =1378.2.

We claim:

1. In a process of linking nucelosides with a siloxane bridge of the formula

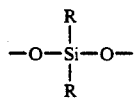

wherein each R is independently C1–C6 alkyl; comprising reacting a 3'-silylated-5'-protected necleoside with an O-unprotected nucleoside, the improvement which comprises performing said reaction in the presence of a sterically hindered base catalyst.

2. The process according to claim 1 wherein each R is independently isopropyl or methyl.

3. The process according to claim 1 wherein both the silylated nucleoside and the unprotected nucleoside are monomeric nucleosides.

4. The process according to claim 3 wherein the monomeric nucleosides are independently selected from thymidine, N$^6$-benzoyldeoxyadenosine, N$^4$-benzoyldeoxycytidine and N$^2$-isobutyldeoxyguanosine.

5. The process according to claim 1 wherein the silylated nucleoside is the 3'-terminal nucleoside of an oligonucleotide or oligonucleotide analog.

6. The process according to claim 1 wherein the unprotected nucleoside is the 5'-terminal nucleoside of an oligonucleotide or oligonucleotide analog in which both the 3'- and 5'- terminal nucleosides are unprotected.

7. The process according to claim 1 wherein the reaction occurs in an aprotic solution.

8. The process according to claim 7 wherein the aprotic solution comprises 2,6-di-tert-butyl-4-methylpyridine in a mixture of acetonitrile and dimethylformamide.

9. The process according to claim 1 wherein the base catalyst is 2,6-di-tert-butyl-4-methylpyridine.

10. An improved process of synthesizing an oligonucleotide analog having siloxane internucleoside linkages comprising the steps of:
a) silylating a 5'-protected nucleoside with a bifunctional silylating reagent of the formula:

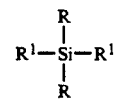

wherein each R is independently C$_1$–C$_6$ alkyl and each R$^1$ is a leaving group;
b) wherein the improvement comprises reacting the silylated nucleoside with an unprotected nucleoside in the presence of a sterically hindered base catalyst; and
c) repeating steps a) and b) to form said oligonucleotide analog.

11. The process according to claim 10 wherein both the silylated nucleoside and the unprotected nucleoside are monomeric nucleosides.

12. The process according to claim 11 wherein the monomeric nucleosides are independently thymidine, N$^6$-benzoyldeoxyadenosine, N$^4$-benzoyldeoxycytidine or N$^2$-isobutyldeoxyguanosine.

13. The process according to claim 10 wherein the silylated nucleoside is the 3'-terminal nucleoside of an oligonucleotide or oligonucleotide analog.

14. The process according to claim 10 wherein the unprotected nucleoside is the 5'-terminal nucleoside of an oligonucleotide or an oligonucleotide analog in which both the 3' and 5' terminal nucleosides are unprotected.

15. The process according to claim 10 wherein reacting occurs in a neutral or alkaline, aprotic solution.

16. The process according to claim 10 wherein the base catalyst is 2,6-di-tert-butyl-4-methylpyridine.

17. The process according to claim 10 wherein each R$^1$ is Cl or SO$_2$CF$_3$.

18. The process according to claim 10 wherein each R is independently isopropyl or methyl and each R$^1$ is independently Cl or SO$_2$CF$_3$.

19. An improved process of synthesizing oligonucleotide analogs having siloxane internucleoside linkages comprising the steps of:

a) deprotecting a 5'-protected nucleoside attached to a solid support;

b) wherein the improvement comprises reacting the deprotected nucleoside with a 3'-silylated-5'-protected nucleoside in the presence of a hindered base catalyst in a neutral or basic aprotic solvent;

c) capping unreacted nucleosides;

d) repeating steps a), b and c) until an oligonucleotide analog of desired length is formed; and e) removing the formed oligonucleotide analog from the solid support.

20. The process according to claim 19 wherein the siloxane internucleoside linkage has the formula:

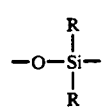

where R is independently $C_1$–$C_6$ alkyl.

21. The process according to claim 20 wherein R is isopropyl or methyl.

22. The process according to claim 19 wherein the hindered base is 2,6-di-tert-butyl-4-methyl-pyridine.

23. The process according to claim 19 wherein the solvent is a mixture of acetonitrile and dimethylformamide.

24. The process according to claim 19 wherein the removing step is accomplished by contacting the product of step b with aqueous ammonia in isopropanol and acetonitrile.

* * * * *